United States Patent [19]

Miyazaki

[11] Patent Number: 5,843,695
[45] Date of Patent: Dec. 1, 1998

[54] METHOD FOR DECOMPOSING AMYLOID PROTEIN PRECURSOR AND AMYLOID β-PROTEIN

[75] Inventor: Kaoru Miyazaki, Kanagawa-ken, Japan

[73] Assignee: Oriental Yeast Co., Ltd., Tokyo, Japan

[21] Appl. No.: 641,774

[22] Filed: Apr. 30, 1996

Related U.S. Application Data

[62] Division of Ser. No. 232,474, Apr. 25, 1994, abandoned.

[30] Foreign Application Priority Data

Apr. 27, 1993 [JP] Japan .................................. 5-122207
Feb. 25, 1994 [JP] Japan .................................. 6-051133

[51] Int. Cl.$^6$ ........................................................ C12Q 1/37
[52] U.S. Cl. .................................................. 435/23; 435/4
[58] Field of Search ................................ 424/94.6, 94.2, 424/94.67, 94.63; 435/4, 7.2, 7.4, 23; 514/879, 2, 12, 21

[56] References Cited

U.S. PATENT DOCUMENTS 4,902,680  2/1990  Aroonsakul ............................ 514/171
5,221,607  6/1993  Cordell et al. .
5,252,463  10/1993  Nelson et al. .

FOREIGN PATENT DOCUMENTS 9203542  3/1992  WIPO .

OTHER PUBLICATIONS

Ezzel, *Science News*, vol. 141, pp. 152–153, 1992.
Miyazaki et al, *Biochemical and Biophysical Research Communications*, vol. 185, No. 3, Jun. 30, 1992.
Miyazaki et al, *Nature*, vol. 362, pp. 839–841, Apr. 29, 1993.
Walsh, D.M., et al., "An Investigation into the Proteolytic Cleavage of Alzheimer Amyloid Precursor Protein in PC–12 Cells", *Biochemical Society Transactions*, vol. 22, No. 1, p. 14S, 1994.
K. Miyazaki et al. "Activation of TIMP–2/Progelatinase A Complex by Stromelysin," Biochemical and Biophysical Research Communications. vol. 185, No. 3, 1992. Jun. 30, 1992.
Hansjorg Kolkenbrock et al. "The complex between a tissue inhibitor of metalloproteinases (TIMP–2) and 72–kDa progelatinase is a metalloproteinase inhibitor," Eur. J. Biochem. 198, 775–781 (1991).
K. Miyazaki et al. "Gelatinase A and APP." Nature. vol. 368. 21 Apr. 1994.

*Primary Examiner*—Paula K. Hutzell
*Assistant Examiner*—Patricia A. Duffy
*Attorney, Agent, or Firm*—Browdy and Neimark

[57] ABSTRACT

The present invention relates to a βAP decomposing agent or a medicine for preventing and curing Alzheimer's disease, which contains, as the active ingredient, gelatinase A, a limited decomposate of gelatinase A, progelatinase A, a complex to which any of them has bonded or a material containing any of them. βAP is a substance which is considered to cause Alzheimer's disease.

12 Claims, 4 Drawing Sheets

FIG. 1

```
SEQUENCE   770 AA;   86943 MW;   2987728 CN;

18
MLPGLALLLL  AAWTARALEV  PTDGNAGLLA  EPQIAMFCGR  LNMHMNVQNG  KWDSDPSGTK   60
TCIDTKEGIL  QYCQEVYPEL  QITNVVEANQ  PVTIQNWCKR  GRKQCKTHPH  FVIPYRCLVG  120
EFVSDALLVP  DKCKFLHQER  MDVCETHLHW  HTVAKETCSE  KSTNLHDYGM  LLPCGIDKFR  180
GVEFVCCPLA  EESDNVDSAD  AEEDDSDVWW  GGADTDYADG  SEDKVVEVAE  EEEVAEVEEE  240
                                                       289
EADDDEDDED  GDEVEEEAEE  PYEEATERTT  SIATTTTTT   ESVEEVVREV  CSEQAETGPC  300
                                                     345
RAMISRWYFD  VTEGKCAPFF  YGGCGGNRNN  FDTEEYCMAV  CGSAMSQSLL  KTTQEPLARD  360
  363
PVKLPTTAAS  TPDAVDKYLE  TPGDENEHAH  FQKAKERLEA  KHRERMSQVM  REWEEAERQA  420
              439
KNLPKADKKA  VIQHFQEKVE  SLEQEAANER  QQLVETHMAR  VEAMLNDRRR  LALENYITAL  480
QAVPPRPRHV  FNMLKKYVRA  EQKDRQHTLK  HFEHVRMVDP  KKAAQIRSQV  MTHLRVIYER  540
MNQSLSLLYN  VPAVAEEIQD  EVDELLQKEQ  NYSDDVLANM  ISEPRISYGN  DALMPSLTET  600
KTTVELLPVN  GEFSLDDLQP  WHSFGADSVP  ANTENEVEPV  DARPAADRGL  TTRPGSGLTN  660
IKTEEISEVK  MDAEFRHDSG  YEVHHQKLVF  FAEDVGSNKG  AIIGLMVGGV  VIATVIVITL  720
                           687                                 770
VMLKKQYTS   IHHGVVEVDA  AVTPEERHLS  KMQQNGYENP  TYKFFEQMQN
```

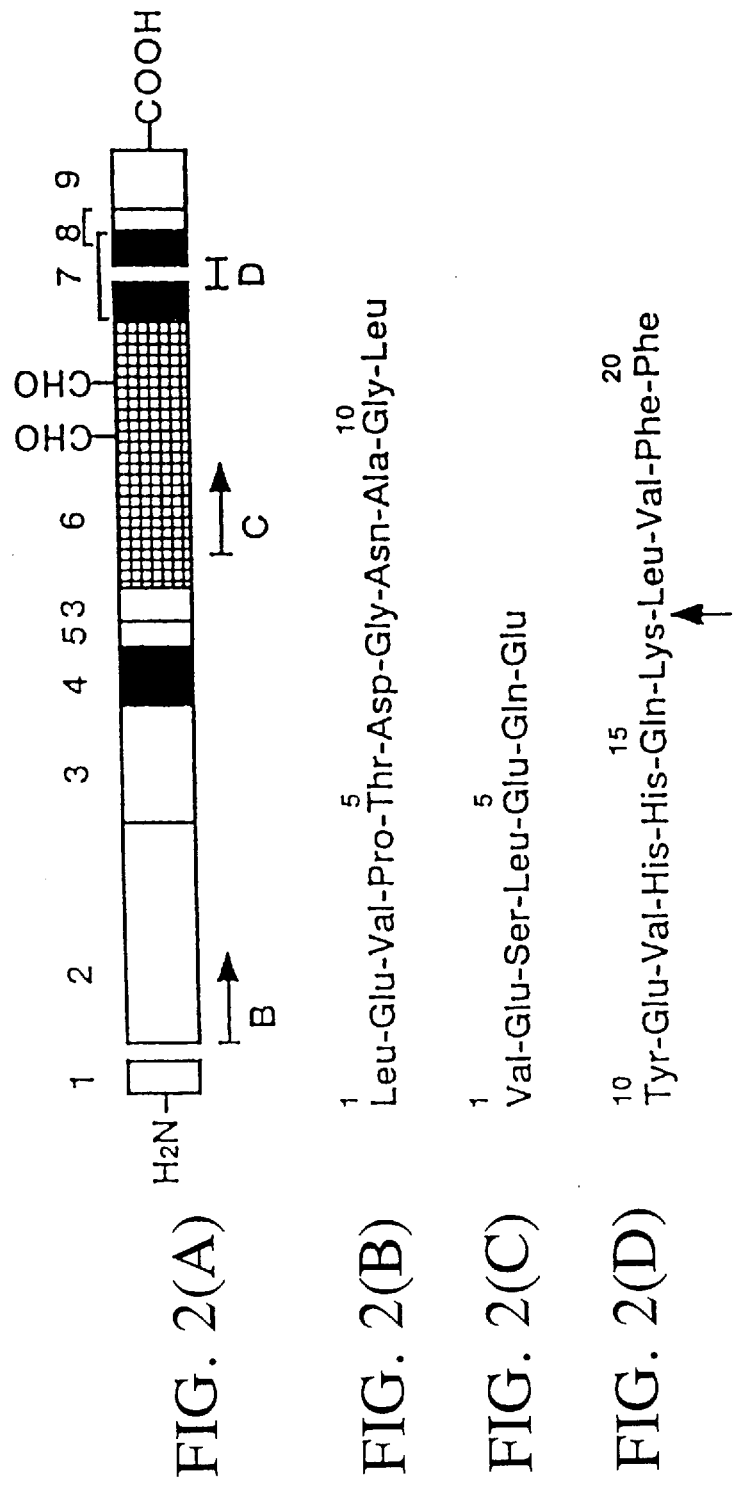

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 770 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met  Leu  Pro  Gly  Leu  Ala  Leu  Leu  Leu  Leu  Ala  Ala  Trp  Thr  Ala  Arg
1                   5                        10                       15

Ala  Leu  Glu  Val  Pro  Thr  Asp  Gly  Asn  Ala  Gly  Leu  Leu  Ala  Glu  Pro
               20                       25                       30

Gln  Ile  Ala  Met  Phe  Cys  Gly  Arg  Leu  Asn  Met  His  Met  Asn  Val  Gln
          35                       40                  45

Asn  Gly  Lys  Trp  Asp  Ser  Asp  Pro  Ser  Gly  Thr  Lys  Thr  Cys  Ile  Asp
     50                  55                       60

Thr  Lys  Glu  Gly  Ile  Leu  Gln  Tyr  Cys  Gln  Glu  Val  Tyr  Pro  Glu  Leu
65                       70                  75                            80

Gln  Ile  Thr  Asn  Val  Val  Glu  Ala  Asn  Gln  Pro  Val  Thr  Ile  Gln  Asn
                    85                  90                       95

Trp  Cys  Lys  Arg  Gly  Arg  Lys  Gln  Cys  Lys  Thr  His  Pro  His  Phe  Val
               100                      105                      110

Ile  Pro  Tyr  Arg  Cys  Leu  Val  Gly  Glu  Phe  Val  Ser  Asp  Ala  Leu  Leu
               115                 120                 125

Val  Pro  Asp  Lys  Cys  Lys  Phe  Leu  His  Gln  Glu  Arg  Met  Asp  Val  Cys
     130                      135                 140

Glu  Thr  His  Leu  His  Trp  His  Thr  Val  Ala  Lys  Glu  Thr  Cys  Ser  Glu
145                      150                      155                      160

Lys  Ser  Thr  Asn  Leu  His  Asp  Tyr  Gly  Met  Leu  Leu  Pro  Cys  Gly  Ile
               165                      170                      175

Asp  Lys  Phe  Arg  Gly  Val  Glu  Phe  Val  Cys  Cys  Pro  Leu  Ala  Glu  Glu
               180                      185                      190

Ser  Asp  Asn  Val  Asp  Ser  Ala  Asp  Ala  Glu  Glu  Asp  Asp  Ser  Asp  Val
```

-continued

|     |     |     | 195 |     |     |     | 200 |     |     |     | 205 |     |     |     |
| --- | --- | --- | --- | --- | --- | --- | --- | --- | --- | --- | --- | --- | --- | --- |
| Trp | Trp | Gly | Gly | Ala | Asp | Thr | Asp | Tyr | Ala | Asp | Gly | Ser | Glu | Asp | Lys |
|     | 210 |     |     |     |     | 215 |     |     |     |     | 220 |     |     |     |
| Val | Val | Glu | Val | Ala | Glu | Glu | Glu | Val | Ala | Glu | Val | Glu | Glu | Glu |
| 225 |     |     |     |     | 230 |     |     |     |     | 235 |     |     |     | 240 |
| Glu | Ala | Asp | Asp | Asp | Glu | Asp | Asp | Glu | Asp | Gly | Asp | Glu | Val | Glu | Glu |
|     |     |     |     | 245 |     |     |     |     | 250 |     |     |     |     | 255 |
| Glu | Ala | Glu | Glu | Pro | Tyr | Glu | Glu | Ala | Thr | Glu | Arg | Thr | Thr | Ser | Ile |
|     |     |     | 260 |     |     |     |     | 265 |     |     |     |     | 270 |     |
| Ala | Thr | Thr | Thr | Thr | Thr | Thr | Glu | Ser | Val | Glu | Val | Val | Arg |
|     |     | 275 |     |     |     |     | 280 |     |     |     |     | 285 |     |
| Glu | Val | Cys | Ser | Glu | Gln | Ala | Glu | Thr | Gly | Pro | Cys | Arg | Ala | Met | Ile |
|     |     | 290 |     |     |     |     | 295 |     |     |     |     | 300 |     |     |
| Ser | Arg | Trp | Tyr | Phe | Asp | Val | Thr | Glu | Gly | Lys | Cys | Ala | Pro | Phe | Phe |
| 305 |     |     |     |     | 310 |     |     |     |     | 315 |     |     |     |     | 320 |
| Tyr | Gly | Gly | Cys | Gly | Gly | Asn | Arg | Asn | Asn | Phe | Asp | Thr | Glu | Glu | Tyr |
|     |     |     |     | 325 |     |     |     |     | 330 |     |     |     |     | 335 |
| Cys | Met | Ala | Val | Cys | Gly | Ser | Ala | Met | Ser | Gln | Ser | Leu | Leu | Lys | Thr |
|     |     |     | 340 |     |     |     |     | 345 |     |     |     |     | 350 |     |
| Thr | Gln | Glu | Pro | Leu | Ala | Arg | Asp | Pro | Val | Lys | Leu | Pro | Thr | Thr | Ala |
|     |     | 355 |     |     |     |     | 360 |     |     |     |     | 365 |     |     |
| Ala | Ser | Thr | Pro | Asp | Ala | Val | Asp | Lys | Tyr | Leu | Glu | Thr | Pro | Gly | Asp |
|     |     | 370 |     |     |     |     | 375 |     |     |     |     | 380 |     |     |
| Glu | Asn | Glu | His | Ala | His | Phe | Gln | Lys | Ala | Lys | Glu | Arg | Leu | Glu | Ala |
| 385 |     |     |     |     | 390 |     |     |     |     | 395 |     |     |     |     | 400 |
| Lys | His | Arg | Glu | Arg | Met | Ser | Gln | Val | Met | Arg | Glu | Trp | Glu | Glu | Ala |
|     |     |     |     | 405 |     |     |     |     | 410 |     |     |     |     | 415 |
| Glu | Arg | Gln | Ala | Lys | Asn | Leu | Pro | Lys | Ala | Asp | Lys | Lys | Ala | Val | Ile |
|     |     |     | 420 |     |     |     |     | 425 |     |     |     |     | 430 |     |
| Gln | His | Phe | Gln | Glu | Lys | Val | Glu | Ser | Leu | Glu | Gln | Glu | Ala | Ala | Asn |
|     |     | 435 |     |     |     |     | 440 |     |     |     |     | 445 |     |     |
| Glu | Arg | Gln | Gln | Leu | Val | Glu | Thr | His | Met | Ala | Arg | Val | Glu | Ala | Met |
|     |     | 450 |     |     |     |     | 455 |     |     |     |     | 460 |     |     |
| Leu | Asn | Asp | Arg | Arg | Arg | Leu | Ala | Leu | Glu | Asn | Tyr | Ile | Thr | Ala | Leu |
| 465 |     |     |     |     | 470 |     |     |     |     | 475 |     |     |     |     | 480 |
| Gln | Ala | Val | Pro | Pro | Arg | Pro | Arg | His | Val | Phe | Asn | Met | Leu | Lys | Lys |
|     |     |     |     | 485 |     |     |     |     | 490 |     |     |     |     | 495 |
| Tyr | Val | Arg | Ala | Glu | Gln | Lys | Asp | Arg | Gln | His | Thr | Leu | Lys | His | Phe |
|     |     |     | 500 |     |     |     |     | 505 |     |     |     |     | 510 |     |
| Glu | His | Val | Arg | Met | Val | Asp | Pro | Lys | Lys | Ala | Ala | Gln | Ile | Arg | Ser |
|     |     | 515 |     |     |     |     | 520 |     |     |     |     | 525 |     |     |
| Gln | Val | Met | Thr | His | Leu | Arg | Val | Ile | Tyr | Glu | Arg | Met | Asn | Gln | Ser |
|     |     | 530 |     |     |     |     | 535 |     |     |     |     | 540 |     |     |
| Leu | Ser | Leu | Leu | Tyr | Asn | Val | Pro | Ala | Val | Ala | Glu | Glu | Ile | Gln | Asp |
| 545 |     |     |     |     | 550 |     |     |     |     | 555 |     |     |     |     | 560 |
| Glu | Val | Asp | Glu | Leu | Leu | Gln | Lys | Glu | Gln | Asn | Tyr | Ser | Asp | Asp | Val |
|     |     |     |     | 565 |     |     |     |     | 570 |     |     |     |     | 575 |
| Leu | Ala | Asn | Met | Ile | Ser | Glu | Pro | Arg | Ile | Ser | Tyr | Gly | Asn | Asp | Ala |
|     |     |     | 580 |     |     |     |     | 585 |     |     |     |     | 590 |     |
| Leu | Met | Pro | Ser | Leu | Thr | Glu | Thr | Lys | Thr | Thr | Val | Glu | Leu | Leu | Pro |
|     |     | 595 |     |     |     |     | 600 |     |     |     |     | 605 |     |     |
| Val | Asn | Gly | Glu | Phe | Ser | Leu | Asp | Asp | Leu | Gln | Pro | Trp | His | Ser | Phe |
| 610 |     |     |     |     | 615 |     |     |     |     | 620 |     |     |     |     |

| | | | | | | | | | | | | | | |
|---|---|---|---|---|---|---|---|---|---|---|---|---|---|---|
| Gly 625 | Ala | Asp | Ser | Val | Pro 630 | Ala | Asn | Thr | Glu | Asn 635 | Glu | Val | Glu | Pro | Val 640 |
| Asp | Ala | Arg | Pro | Ala 645 | Ala | Asp | Arg | Gly | Leu 650 | Thr | Thr | Arg | Pro | Gly 655 | Ser |
| Gly | Leu | Thr | Asn 660 | Ile | Lys | Thr | Glu | Glu 665 | Ile | Ser | Glu | Val | Lys 670 | Met | Asp |
| Ala | Glu | Phe 675 | Arg | His | Asp | Ser | Gly 680 | Tyr | Glu | Val | His | His 685 | Gln | Lys | Leu |
| Val | Phe 690 | Phe | Ala | Glu | Asp | Val 695 | Gly | Ser | Asn | Lys | Gly 700 | Ala | Ile | Ile | Gly |
| Leu 705 | Met | Val | Gly | Gly | Val 710 | Val | Ile | Ala | Thr | Val 715 | Ile | Val | Ile | Thr | Leu 720 |
| Val | Met | Leu | Lys | Lys 725 | Lys | Gln | Tyr | Thr | Ser 730 | Ile | His | His | Gly | Val 735 | Val |
| Glu | Val | Asp | Ala 740 | Ala | Val | Thr | Pro | Glu 745 | Glu | Arg | His | Leu | Ser 750 | Lys | Met |
| Gln | Gln | Asn 755 | Gly | Tyr | Glu | Asn | Pro 760 | Thr | Tyr | Lys | Phe | Phe 765 | Glu | Gln | Met |
| Gln | Asn 770 | | | | | | | | | | | | | | |

METHOD FOR DECOMPOSING AMYLOID PROTEIN PRECURSOR AND AMYLOID β-PROTEIN

This application is a divisional of application Serial No. 08/232,474, filed Apr. 25, 1994, now abandoned.

DETAILED EXPLANATION OF THE INVENTION

The present invention relates to an agent decomposing βAP (amyloid β-protein or A4 protein).

After formation of βAP, its aggregation causes the formation of senile plaques to be seen on the outside of neurocytes in the brain of a patient suffering from Alzheimer's disease (AD). Therefore, the βAP decomposing agent of the present invention is expected to be useful also as a medicine for preventing and curing Alzheimer's disease.

PRIOR ART

In general, Alzheimer's disease is a typical dementia, with which middle-aged or old-aged persons are often attacked, and this causes noticeable dysmnesia and retardation of mental capacity due to denaturation of neurons. Senile plaques appear on the outside of neurons in the brain of a patient suffering from Alzheimer's disease. Senile plaques consist essentially of βAP, in which it is seen that βAP aggregates by itself to form the cores of the plaques and denatured neuraxones surround the cores.

It has not been clarified as yet why βAP is produced to form senile plaques only in patients suffering from Alzheimer's disease. In fact, the formation of senile plaques is not seen in the aged with healthy mental capacity.

It is known that βAP is derived from APP (amyloid protein precursor) which is a cell membrane protein having a molecular weight of about 100,000.

APP is produced by an APP gene, which produces three major forms of related proteins (APP770, APP751, and APP695) due to the difference in the splicing. As one example, APP770 will be illustrated in the drawings attached hereto.

FIG. 2 shows the outline structure of APP770, and its amino acid sequence has already been clarified as shown in FIG. 1.

In FIG. 2, 1 indicates the signal sequence from 1 M (Met), and APP is comprised of 770 amino acids that are sequenced in order. 6 is a glycosylation domain where carbohydrate chains bond to the sequence at two sites, as shown by two CHO's in FIG. 2. In FIG. 2, the domain 8 corresponds to the transmembrane region that has penetrated the plasma membrane.

When APP is cut at the site of D in FIG. 2(A) or, that is, at the arrowed site in the sequence of FIG. 2(D), it causes no disorder; but, in APP, if the part of D is closed to complete the domain 7 as one part (dark area) and the both sides of the domain 7 are cut, then APP liberates βAP (the whole domain 7). βAP is a mixture of peptides having the sequence comprising 1st to 39–43th amino acids (corresponding to amino acid residues 672 through 710–714 of SEQ ID NO:1). FIG. 3 shows the structure of $βAP_{1-40}$ (corresponding to amino acid residues 672–711 of SEQ ID NO:1).

In healthy persons, APP is cut at its center part without forming β-amyloid. However, it has heretofore been unknown at all what will act on the arrowed site in FIG. 2(D) (the site is same as the position of the arrow ② in FIG. 3).

PROBLEMS TO BE SOLVED BY THE INVENTION

The present inventor has considered if the bond between 687K (Lys) and 688L (Leu) in the amino acid sequence of APP770 shown in FIG. 1 may be cut or if the bond between 16K (Lys) and 17L (Leu) in βAP shown in FIG. 3 may be cut more rapidly and more strongly before, during or after the formation of β-amyloid, then Alzheimer's disease may be prevented, retarded or cured.

BRIEF EXPLANATION OF THE DRAWINGS

FIG. 1 shows the amino acid sequence of APP770 by one-letter designation (SEQ ID NO:1).

FIGS. 2(A)–2(D). FIG 2(A) shows the outline of the domain structure of APP770 as well as amino acid sequences corresponding to FIG. 2(B) amino acid residues 18–28, FIG. 2(C) amino acid residues 439–445 and FIG. 3(D) amino acid residues 681–691, of SEQ ID NO:1.

MEANS FOR SOLVING THE PROBLEMS

Considering the above-mentioned problems, the present inventor assiduously studied and has found surprisingly that gelatinase A which decomposes gelatin has the action in question. On the basis of the finding, the inventor has completed the present invention.

The present invention relates to a βAP-decomposing agent containing, as the active ingredient, gelatinase A, a limited decomposate of gelatinase A, progelatinase A, a composite to which any of them has bonded or a material containing any of them.

The present invention also relates to a medicine for preventing and curing Alzheimer's disease, which contains, as the active ingredient, gelatinase A, a limited decomposate of gelatinase A, progelatinase A, a composite to which any of them has bonded or a material containing any of them.

According to the present invention, it has been newly found that gelatinase A, a limited decomposate of gelatinase A having a molecular weight of about 40,000, etc. may cut the center part of βAP or, that is, the bond between 687K (Lys) and 688L (Leu) in the amino acid sequence of APP770 shown in FIG. 1.

Gelatinase A and progelatinase A have heretofore been well known as enzymes to be secreted by many cancer cells, etc.

In the present invention, progelatinase A has been purified as its complex with TIMP-2 (tissue inhibitor of metalloproteinases-2) from a culture of human neuroblastoma cell line T98G by an already reported method (Biochemical and Biophysical Research Communications, Vol. 185, No. 3, 1992, pp. 852–859). The TIMP-2/progelatinase complex was hardly activated by an organo-mercurial p-aminophenylmercuric acetate (APMA) and had an activity of 10% or less of the activity of the activated enzyme not containing TIMP-2. When the complex was incubated with stromelysin in the presence of APMA, the progelatinase moiety having a molecular weight of 64 k was effectively converted into a matured gelatinase A having a molecular weight of 57 k and a small amount of an activated enzyme having a molecular weight of 41 k, with the result that its gelatin-decomposing activity increased about 8 times. (From these results, it was considered that stromelysin is a natural activating agent for TIMP-2-bound progelatinase A.)

In the present invention, all of gelatinase A, a limited decomposate of gelatinase A having a molecular weight of about 40,000, progelatinase A, a complex to which any of them has bonded or a material containing any of them are used as the active ingredients.

EXAMPLE

Progelatinase A not containing TIMP-2 was separated from TIMP-2-bound progelatinase by heparin affinity chromatography in accordance with the Kolkenbrock et al's method. (See Kolkenbrock, H., Orgel, D., Hecker-Kia, A., Noack, W. & Ulbrick, N.; Eur. J. Biochem., 198, 775–781 (1991).)

One μg of progelatinase A was activated by inbubating it in 20 mM of Tris-HCl (pH 7.5) containing 10 mM of $Ca^{++}$, along with 1 mM of APMA and 0.25 μg of rat stromelysin, at 37° C. for one hour.

Figure 4A:
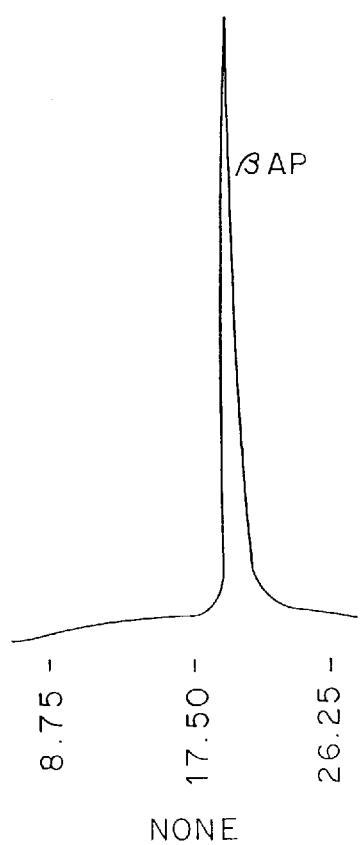
FIGS. 4(A) and 4(B) show the graph of reversed phase HPLC of βAP (FIG. 4(A) decomposed by gelatinase A (FIG. 4(B)).
Figure 4B:
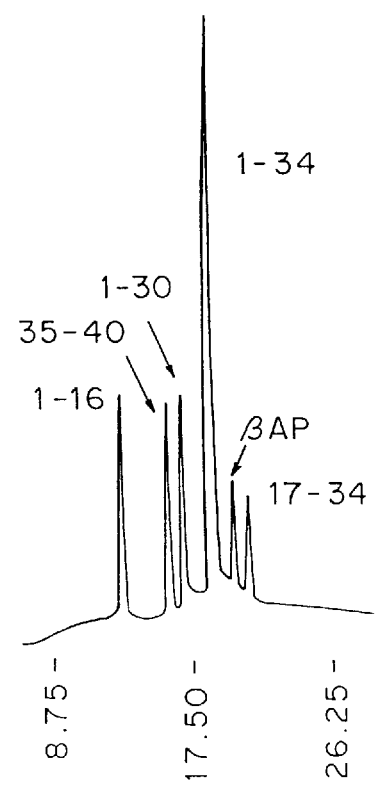

The thus-activated enzyme, gelatinase A was incubated in 50 μl of Tris-HCl/$Ca^{++}$ buffer along with 20 nmol of a synthetic βAP peptide ($βAP_{1-40}$), at 37° C. for 6 hours, mixed with 0.5 ml of 0.05% trifluoroacetic acid (TFA) and applied to Cosmosil 5c18 reversed phase HPLC column (4.6×150 mm) (made by Nacalai Tesque, Kyoto, Japan). The charged column was subjected to linear gradient elution, using an eluent of from 0 to 80% acetonitrile in 15 ml of 0.05% TFA at a flow rate of 0.5 ml/min. The result is shown in FIG. 4(B). As a control, an enzyme-free βAP was incubated under the same condition and applied to the same column. (See FIG. 4(A)).

Figure 3:
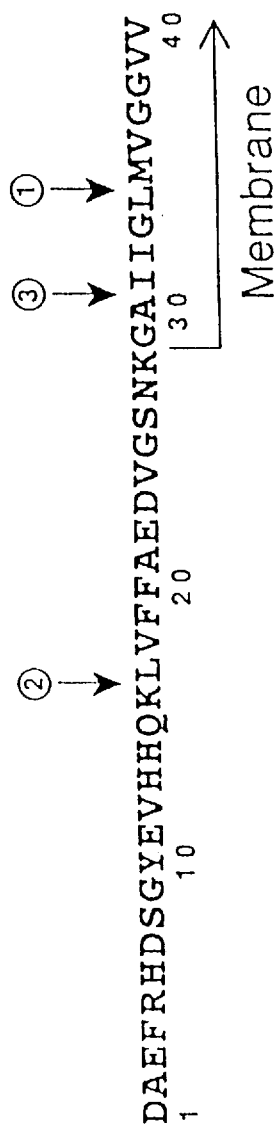
FIG. 3 shows the amino acid sequence corresponding to amino acid residues 672–711 of SEQ ID NO:1, including the cleavage sites of βAP to be cut by gelatinase A.

As is obvious from FIG. 4, βAP was desirably cut by the gelatinase A, at the cleavage sites ①, ② and ③ shown in FIG. 3.

---

I claim:

1. An in vitro method for decomposing amyloid protein precursor, which comprises contacting and decomposing an amyloid protein precursor with a component selected from the group consisting of (1) progelatinase A, (2) gelatinase A having a molecular weight of 57 kilodaltons, (3) a decomposate of progelatinase A having a molecular weight of 41 kilodaltons, (4) a complex of progelatinase A with tissue inhibitor of metalloproteinase-2 (TIMP-2), and (5) a mixture of a gelatinase A having a molecular weight of 57 kilodaltons and a decomposate of progelatinase A having a molecular weight of 41 kilodaltons, in an amount which is sufficient, at a temperature and for a period of time, to decompose said amyloid protein precursor in a buffer solution.

2. The method according to claim 1, wherein said component is progelatinase A.

3. The method according to claim 1, wherein said component is gelatinase A having a molecular weight of 57 kilodaltons.

4. The method according to claim 1, wherein said component is a decomposate of progelatinase A having a molecular weight of 41 kilodaltons.

5. The method according to claim 1, wherein said component is a complex of progelatinase A with tissue inhibitor of metalloproteinase-1 (TIMP-2).

6. The method according to claim 1, wherein said component is a mixture of a gelatinase A having a molecular weight of 57 kilodaltons and a decomposate of progelatinase A having a molecular weight of 41 kilodaltons.

7. An in vitro method for decomposing amyloid β-protein, which comprises contacting and decomposing an amyloid β-protein with a component selected from the group consisting of (1) progelatinase A, (2) gelatinase A having a molecular weight of 57 kilodaltons, (3) a decomposate of progelatinase A having a molecular weight of 41 kilodaltons, (4) a complex of progelatinase A with tissue inhibitor of metalloproteinase-2 (TIMP-2), and (5) a mixture of a gelatinase A having a molecular weight of 57 kilodaltons and a decomposate of progelatinase A having a molecular weight of 41 kilodaltons, in an amount which is sufficient, at a temperature and for a period of time, to decompose said amyloid β-protein in a buffer solution.

8. The method according to claim 7, wherein said component is progelatinase A.

9. The method according to claim 7, wherein said component is gelatinase A having a molecular weight of 57 kilodaltons.

10. The method according to claim 7, wherein said component is a decomposate of progelatinase A having a molecular weight of 41 kilodaltons.

11. The method according to claim 7, wherein said component is a complex of progelatinase A with tissue inhibitor of metalloproteinase-1 (TIMP-2).

12. The method according to claim 7, wherein said component is a mixture of a gelatinase A having a molecular weight of 57 kilodaltons and a decomposate of progelatinase A having a molecular weight of 41 kilodaltons.

* * * * *